United States Patent [19]

Boron

[11] 4,206,651

[45] Jun. 10, 1980

[54] SLIDING SLEEVE SAMPLER

[75] Inventor: Joseph J. Boron, Medina, Ohio
[73] Assignee: Rossborough Manufacturing Co., Avon Lake, Ohio
[21] Appl. No.: 964,931
[22] Filed: Nov. 30, 1978
[51] Int. Cl.² .............................................. G01N 1/12
[52] U.S. Cl. .............................................. 73/425.4 R
[58] Field of Search ...................... 73/425.4 R, DIG. 9

[56] References Cited

U.S. PATENT DOCUMENTS

| 3,859,857 | 1/1975 | Falk | 73/DIG. 9 |
| 4,002,074 | 1/1977 | Collins | 73/DIG. 9 |
| 4,108,003 | 8/1978 | McDevitt | 73/425.4 R |

Primary Examiner—S. Clement Swisher
Attorney, Agent, or Firm—Fay & Sharpe

[57] ABSTRACT

An apparatus for taking samples of molten metal and having provision for a sample tagging member. The preferred embodiment comprises a sampler including a plurality of separable mold forming elements which cooperate to form a mold chamber. The mold forming elements are mounted within a generally cylindrical housing around which is telescoped a second generally cylindrical member. The mold forming elements are provided with an opening through which a sample tagging member may be placed and the sample tagging member is bent up and around the outside of the first housing and is secured into position frictionally by being overlaid by the second generally cylindrical member telescoped about the first housing.

3 Claims, 5 Drawing Figures

SLIDING SLEEVE SAMPLER

BACKGROUND OF THE INVENTION

This invention relates to apparatus for obtaining a sample of molten metal. Such apparatus is generally to be found in the U.S. Patent and Trademark Office Subclasses relating to measuring and testing, sampler, and toller implements.

SUMMARY OF THE INVENTION

The subject invention provides an improved construction for a device permitting identification of samples being taken from molten metal. Sampling devices formed in accordance with the invention are structured so as to permit interchangeability of tagging members quickly and efficiently prior to immersion of the sampler into either the stream or the bath of molten metal being sampled. The instant invention may be utilized with mold chambers having a variety of configurations.

In particular, the invention comprises apparatus which is capable of securely containing mold forming elements which may be slideable within a sleeve. Telescoped over the sleeve containing the mold forming elements is a second containment member generally made from cardboard or the like. The mold forming elements are designed such that an aperture is available for the insertion of a tagging member. It is contemplated that the tagging member be bent around to the outside of the first housing member and then overlaid with the second telescoped member to hold it securely in position.

In addition to holding the tagging member in position, the second telescoped member provides protection for the identification appearing on the tag itself.

More specific aspects of the invention contemplate that the mold chambers defined by the mold forming elements may be of virtually any configuration. In one alternative embodiment, the mold forming elements provide baffle members for helping to contain material within the mold chambers as the material is freezing upon withdrawal from the bath or stream of molten metal being sampled.

Accordingly, the primary object of the invention is the provision of an apparatus for identifying samples of molten metal.

Another object is the provision of an identification structure that accomodates quick interchangeability of identification members.

A third object is the provision of a protective sleeve to protect the identification portion of the tagging member from disfiguration during immersion in the bath being sampled.

The above and other objects and advantages all will become more readily apparent when the accompanying drawings are viewed in light of the following description.

DESCRIPTION OF THE PRIOR ART

The sampling apparatus of the prior art which had provision for the attachment of a tagging identification member generally were constructed in such a manner that changing or removal of the tagging member prior to immersion was extremely difficult, if not impossible. This has been because the tagging member was designed to be held within the mold chamber by the interaction of the mold chamber and various bends or configurations of the tagging member.

Identification of the metal or sample being taken was sometimes printed on the tagging member positioned between the mold forming elements. In other prior art embodiments, the tagging device was provided with a loop through which an identification tag could be affixed.

Further prior art devices were designed such that a piece of wire would become molded within the sample being taken upon freezing of the sample. Spacers which separated the mold halves to allow air to escape during immersion of the sampler have also been used for labeling purposes.

The difficulty encountered with the prior devices was that it was cumbersome and time consuming to replace the sample identification or tagging member on the job site. In fact, in many of the prior devices, this was virtually impossible without destroying the mold itself.

DESCRIPTION OF THE PREFERRED EMBODIMENT

Figure 1:
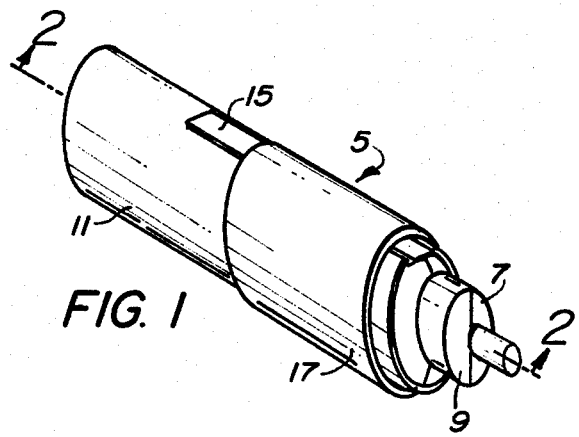
FIG. 1 is a perspective view of the sampling apparatus.
Figure 3:
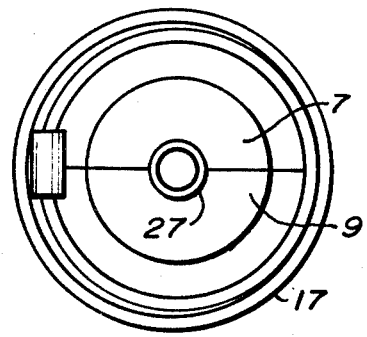
FIG. 3 is a view taken along line 33 of FIG 2.
Figure 4:
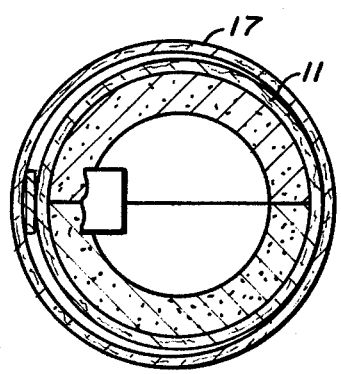
FIG. 4 is a view taken along line 44 of FIG. 2.

Referring now more particularly to the drawings wherein the showings are for the purpose of illustrating preferred embodiments of the invention only, and not for the purpose of limiting the same, FIG. 1 shows a sampling apparatus 5 formed in accordance with the instant invention.

The apparatus is comprised of separable mold forming elements 7 and 9 which are slidably located within a first housing 11. A sample tagging member 15 which extends from outside of housing 11 to the interior of the mold sections is held in place by a second housing 17 telescoped about the first housing 11.

Figure 2:
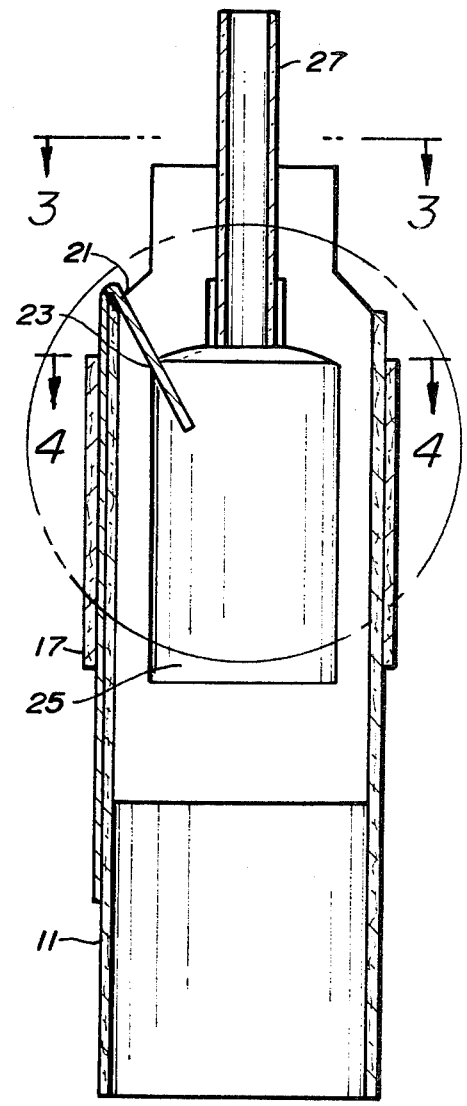
FIG. 2 is an enlarged cross-sectional view taken along line 22 of FIG. 1.

Referring to FIG. 2, it will be seen that the tagging member 15 enters through a slot 21 in the upper portion of the separable mold forming elements. At point 23, the tagging member enters the mold chamber 25 and extends a slight distance into the chamber. When the apparatus is in use, molten metal enters entry tube 27 and proceeds into the mold chamber 25 where, after solidification, the tagging member is frozen into the sample.

It can be seen that the tagging member can be readily changed at the sampling site since it is only frictionally secured by the second housing 17. This facilitates the customizing of the sampling apparatus for such things as melt identification, sample number, furnace or plant number, etc. It will be appreciated, and is known in the art, that the mold chamber itself can be configured in a number of different manners to provide the desired sample for testing and analytical purposes.

Figure 5:
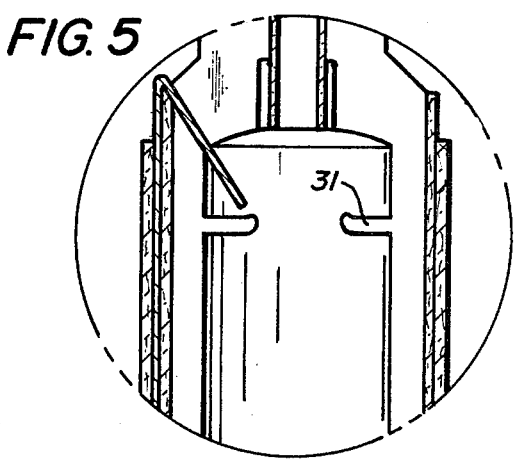
FIG. 5 is a view taken generally in the area of the circle portion of FIG. 2 and shows an alternative embodiment of the internal configuration of the mold chamber.

In FIG. 5, it will be noted that an alternative embodiment of the configuration of the inside of the mold chamber is shown in which a baffle 31 is provided. This baffle aids in preventing the escape of molten material when the sampler is withdrawn from the molten metal which is being tested. This is especially useful in helping to eliminate voids while the sample is freezing.

Along these same lines, it may be desirable for the internal cavity to have flats on one or both sides for forming samples which facilitate clamping the sample obtained into a vice for drilling or cutting.

Regardless, however, of the desired internal configuration of the mold cavity, it can be seen that during shipment the mold halves 7 and 9 can be contained entirely within the housing 11 so that the sample entry conduit 27 is protected. Upon arrival at the site, the mold segments can be pushed forward and a suitably marked tagging member 15 inserted in the aperture provided in the mold segments. The second housing 17 then can be slid over the tagging member to hold it securely in place. During shipment, of course, all parts are shipped in one package and due to the slidable features of the elements comprising the apparatus various tagging members can be readily substituted.

Having described my invention, it is to be understood that various other embodiments can be utilized without departing from the scope of my invention.

What is claimed is:

1. In an apparatus for taking a sample of molten metal and including a plurality of separable mold forming elements which cooperate to form a mold chamber and wherein said mold forming elements are mounted within a first containment member, the improvement comprising:
    a second member slideably engaging and telescoped around said first member; and,
    a sample tagging member being removably secured by and between said first containment member and said second member and extending into said mold chamber.

2. The improvement of claim 1 wherein said first containment member and said second member are generally cylindrical.

3. In an apparatus for taking a sample of molten metal including a mold forming element defining a mold chamber mounted in a housing, the improvement comprising:
    a tagging member extending from within said mold chamber to the outside of said housing; and
    a tagging member containment sleeve surrounding said housing and releasably engaging said tagging member for positioning a portion of said tagging member outside said housing and within said mold chamber.

* * * * *